United States Patent [19]

Saitoh et al.

[11] Patent Number: 4,775,667

[45] Date of Patent: Oct. 4, 1988

[54] TOPICAL ANALGESIC ANTI-INFLAMMATORY COMPOSITION

[75] Inventors: Izumi Saitoh, Hyogo; Hirokuni Jyoyama; Fujio Asanuma, both of Nara; Katsumi Hirose, Osaka; Shohei Egawa, Hyogo, all of Japan

[73] Assignee: Shionogi & Co., Ltd., Osaka, Japan

[21] Appl. No.: 911,151

[22] Filed: Sep. 24, 1986

[30] Foreign Application Priority Data

Sep. 26, 1985 [JP] Japan ............................. 60-214272

[51] Int. Cl.⁴ ................... A61K 31/045; A61K 31/60; A61K 31/605
[52] U.S. Cl. .................... 514/160; 514/164; 514/724; 514/729
[58] Field of Search ............... 514/729, 724, 160, 164

[56] References Cited

FOREIGN PATENT DOCUMENTS 48-03364 1/1973 Japan.
57-206610 12/1982 Japan.

Primary Examiner—Stanley J. Friedman
Attorney, Agent, or Firm—Birch, Stewart, Kolasch & Birch

[57] ABSTRACT

Topical analgesic anti-inflammatory compositions containing a corticosteroid in addition to the conventional efficacy-proven ingredients are disclosed. They may be embodied in an aerosol, a solution and any other type of composition being convenient for administration. More than the sum of effects of the individual ingredients has been proved. In other words, the effects of the salicylate esters and L-menthol are synergistically enhanced by the addition of the corticosteroid. Particularly, the persistency of the analgesic/anti-inflammatory effects of the conventional ingredients has been proved to be dependent upon the the concentration of the corticosteroid in the composition.

15 Claims, 1 Drawing Sheet

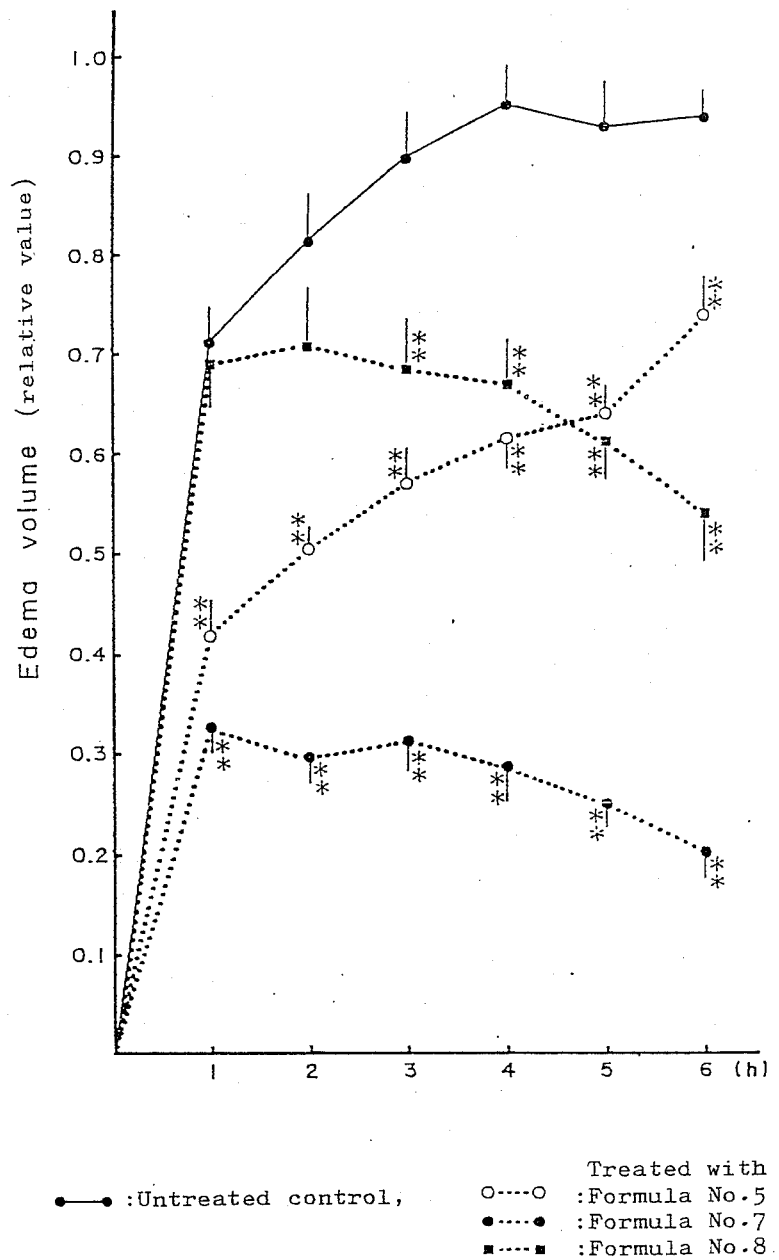

TOPICAL ANALGESIC ANTI-INFLAMMATORY COMPOSITION

BACKGROUNDS OF THE INVENTION

1. Field of the Invention

The present invention relates to a topical analgesic anti-inflammatory composition. Particularly, it is concerned with a topical analgesic anti-inflammatory composition of aerosol, solution or the other type which contains a corticosteroid and is able to demonstrate analgesic and/or anti-inflammatory effect that lasts a relatively long time, on sites beneath the skin where the composition is applied.

2. Description of the Prior Art

In the past, it has been a general belief that a topical composition containing a corticosteroid is only effective for rashes on the surface of skin, e.g., such inflammations as eczema and urticaria and that the composition hardly demonstrates an effect to alleviate contusion or myalgia.

There have been conventional topical analgesic anti-inflammatory compositions for contusion or myalgia in the form of an ointment or plaster which contains salicylate esters, menthol and the like as its active ingredients. Some compositions of the aerosol type, containing the same or the like ingredients, are also on the market but these aerosols cannot demonstrate analgesic anti-inflammatory effects persistently.

SUMMARY OF THE INVENTION

The present inventors have found that the analgesic anti-inflammatory effect of the known composition, containing salicylate esters and menthol as its active ingredients, is synergistically enhanced and the effect persists for a long time when small amount of a corticosteroid is incorporated into the composition, and have completed the present invention.

According to the present invention, there is provided a topical analgesic anti-inflammatory composition which contains ethylene glycol monosalycilate, a corticosteroid and L-menthol as its active ingredients. The corticosteroid can generally be exemplified as dexamethasone, prednisolone, methyl prednisolone, hydrocortisone, betamethasone, triamcinolone and esters thereof. Dexamethasone acetate is preferred. Tocopherol acetate which can enhance the anti-inflammatory effect by relaxing the peripheral vascular system may be incorporated into the topical analgesic anti-inflammatory composition.

The disclosed composition may preferably be formed by adding 0.02–5 parts by weight of dexamethasone acetate to a conventional one including 2–100 parts of ethylene glycol salicylate, 10–100 parts of L-menthol and 1–20 parts by weight of tocopherol acetate. The obtained concentrated solution may itself be satisfactory for the topical use and sufficiently effective as intended.

Although any liquefying agent or solvent may not neccessarily be incorporated, the agent may sometimes be of use in order to lower the viscosity of the composition to facilitate spraying or spreading and may serve to prevent some ingredients in the concentrated solution from crystallizing during storage at a low temperature. The liquefying agent may be exemplified as ethanol, isopropanol, trichlorotrifluoroethane (trade name: Freon R 113), gylcerol, propylene glycol and polyethylene glycol (200–600).

The liquefying agents may preferably be used scantily and the addition of 0.1–0.5 part by weight to one part of the concentrated solution is sufficient for fulfilling the intended objects. In the use of lower alkanols, it should be borne in mind that their hydroxyl group might sometimes affect the stability of the essential ingredients adversely.

In embodying the present invention in a plaster, the disclosed concentrated solution should be included in at least one of the layers which constitute the plaster. In general, it is usually dispersed evenly or dissolved in an adhesive layer which may be exemplified as the conventional gum base, polyisobuthylene or variety of silicones of compounded paste. The resultant paste is applied to be spread over a sheet of cloth or polymer film to give the plaster.

In embodying the present invention in the form of an aerosol, the disclosed composition may be hermetically sealed in a spraying container with a non-toxic propellant. The propellant may be exemplified as trichlorofluoromethane (Freon 11), dichlorodifluoromethane (Freon 12), liquified petroleum gas (LPG), methylene chloride and any mixture thereof.

A preferred composition of the aerosol type comprises ethylene glycol monosalicylate in 0.1–5.0 w/w %, dexamethasone acetate in 0.001–0.25 w/w %, L-menthol in 0.5–5.0 w/w %, tocopherol acetate in 0.05–1.0 w/w %, at least one of pharmaceutically acceptable excipients in 0.01–0.5 w/w % and a non toxic propellant of the amount to make the whole 100 w/w %. Ethanol may be included in the composition in 5–20 w/w%, if the aerosol is not exposed to exceptionally adverse conditions.

In embodying the present invention in a form of solution, an alkyl ester of $C_{10}$–$C_{16}$ mono- or di-carboxylic acid may be added to the composition. Isopropyl myristate is a preferred alkyl ester of $C_{10}$–$C_{16}$ mono- or di-carboxylic acid and the expected effect may further be enhanced thereby.

A preferred composition of the solution type is in the scope that comprises ethylene glycol monosalycilate in 0.1–5.0 w/w %, dexamethasone acetate in 0.001–0.25 w/w %, L-menthol in 0.5–5.0 w/w %, tocopherol acetate in 0.05–1.0 w/w %, isopropyl myristate in 10–30 w/w %, at least one of pharmaceutically acceptable excipients in 0.01–0.5 w/w % and ethanol of the amount to make the whole 100 w/w %.

The amounts of the ingredients in the illustrated composition are shown for convenience of exemplification but those smaller than lower limit in the scope will not insure the effectiveness while those larger than the higher limit cannot demonstrate the expected effect properly and will not virtually give a practical composition.

The other pharmaceutically acceptable excipients/adjuvants include perfumes, coloring agents, liquefying agent, viscosity enhancing agent, or spreader/sticker, for example, such solid particles as talc, aluminum chloride and titanium dioxide, and may be used in a minute amount whose incorporation does not demonstrate any phisiological activity.

BRIEF DESCRIPTION OF THE DRAWING

The accompanying drawing is a graph showing the effects of the basic composition of the present invention in contrast with the comparative compositions wherein the abscissa represents time and the ordinate represents edema volume (relative value).

DESCRIPTION OF THE PREFERRED EMBODIMENTS

In the followings, the present invention will be elucidated in more detail by way of basic experiments, working and comparative examples.

(1) Confirmation of essential active ingredients:

Aerosols of the formulae listed in Table 1 (numerals in the table represent the amounts of ingredients in grams for 100 ml; each aerosol contains 10 ml of ethanol in common and is hermetically sealed in a gas-tight container with the balance of Freon 11/12, 50:50; the hermetic sealing is applied to the subsequent aerosols in common) are prepared. Each of the aerosols contains one of the already validity-proved analgesic anti-inflammatory ingredient, i.e., salicylate esters (ethylene glycol ester, abbreviate as ES and methyl ester, as MS), L-menthol (LM) and D, L-camphor (C) or contains combinations thereof.

TABLE 1

| Ingredient | Formula | | | | | |
|---|---|---|---|---|---|---|
| | 1 | 2 | 3 | 4 | 5 | 6 |
| ES | 2.00 | | | | 2.00 | 2.00 |
| MS | | 3.00 | | | | |
| LM | | | 3.85 | | 3.85 | |
| C | | | | 3.85 | | 3.85 |

The obtained aerosols are then evaluated in terms of the effect of suppressing edema induced by carragenan (Effect A) and that of suppressing edema induced by contusion (Effect B) in the rat. The results of the evaluation (expressed by mean value for the eight tested rats) are summarized in Table 2. In administering the aerosols, the 4 rats with the edemae are fixed on a stand and the aerosols of the respective Formulae are sprayed on the edemae for 5 seconds by means of spraying nozzles of 600 mg/sec.

The suppressing effects (represented in percent in Effects A and B, in common) are calculated by the formula:

$$(CV - SV)/CV \times 100$$

wherein, CV represents an edema volume of the control rat and SV represents an edema volume of the carragenan-treated or contused rat, (there will also be applied to the other evaluations which will subsequently be described).

TABLE 2

| | Time | Formula | | | | | |
|---|---|---|---|---|---|---|---|
| | | 1 | 2 | 3 | 4 | 5 | 6 |
| Effect A | 2 | 4.7 | 2.3 | −6.8 | −16.4 | 33.0 | 20.4 |
| | 4 | −4.8 | −7.1 | −2.3 | −3.0 | 15.6 | 7.3 |
| | 6 | −4.8 | −10.1 | −7.4 | −3.7 | 6.3 | 3.5 |
| Effect B | 2 | 13.0 | −2.9 | 41.0 | −5.4 | 12.9 | 10.2 |
| | 4 | 13.3 | 0.0 | 31.1 | 2.5 | 29.8 | 15.6 |
| | 6 | 12.6 | 5.3 | 19.6 | 0.0 | 42.0 | 22.4 |

As illustrated in the above table, it is confirmed that any of these aerosols of a single ingredient or of the known combinations thereof cannot demonstrate a satisfactory effect except for Formula 5. Hence, other aerosols (Formulae 7 and 8) were prepared and compared with that of Formula 5 in a similar evaluation. Formula 7 contains 0.01 g of dexamethasone acetate (DA) in addition to the composition of Formula 5 while Formula 8 is of a single ingredient i.e., DA 0.01 g.

The results of the evaluation will be summarized in Table 3 below.

TABLE 3

| | Time (hour) | Formula | | |
|---|---|---|---|---|
| | | 5 | 7 | 8 |
| Effect A | 2 | 33.0 | 46.4 | 8.9 |
| | 4 | 15.6 | 50.1 | 40.6 |
| | 6 | 6.3 | 55.0 | 55.0 |
| Effect B | 2 | 37.4 | 63.2 | 12.9 |
| | 4 | 36.1 | 69.6 | 29.8 |
| | 6 | 20.7 | 78.2 | 42.0 |

From the above results, it is to be noted that the composition of Formula 5 has a high initial effect whereas the low initial effect of Formula 8 will gradually be enhanced as time advances. In contrast to these two compositions, that of Formula 7 has the advantage over both Formulae 5 and 8 and is characterized by having no large difference in the results obtained in the respective evaluations. On this basis it is proved that the effect of the composition of Formula 7 is at least arithmetic addition of those of Formulae 5 and 8 or that the former is such that it could complement the latters.

In order to establish a synergistic effect of the composition of Formula 7 as compared with the compositions of Formulae 5 and 8, the volumes (SV and CV) of edemae induced by contusion are observed to plot the measured values at every hour up to 6 hours to give results shown in the attached drawing.

When ratios of expected decrease in edema volumes of the rats in the administered groups to those of the control groups are given as $\mu_5$, $\mu_8$ and $\mu_7$ (suffixes represent the Formula Number), a hypothesis: $\log \mu_7 = \log \mu_5 + \log \mu_8$, is considered to represent an arithmetic addition.

If the stated hypothesis is rejected by a statistical test (t-test) and a relationship: $\log \mu_7 > \log \mu_5 + \log \mu_8$ is proved, synergism would be established. In an attempt, Table 4 is prepared by conducting such a statistical test on the values of the observed decreases in the edema volumes. As shown in Table 4, the synergistic effects are established at the significance level of 0.05 or less, for all the values at the respective time points except that of the first hour and that of the area under the curve (AUC). Among these, with the values at the time points of 2nd, 4th and 6th hour and with the value of the AUC in particular, the synergisms at the significance level of 0.01 or less are established.

TABLE 4

| Time (hour) | Formula number | Logarithm of relative decrease | | Determination of synergism |
|---|---|---|---|---|
| | | Mean value | Standard error | t-value (significance probability) |
| 1 | 5 | −0.539 | 0.077 | 1.704 |
| | 8 | −0.037 | 0.077 | (0.0516) |
| | 7 | −0.779 | 0.048 | |
| 2 | 5 | −0.477 | 0.052 | 2.894 |
| | 8 | −0.152 | 0.084 | (0.0043) |
| | 7 | −1.042 | 0.103 | |
| 3 | 5 | −0.467 | 0.075 | 2.105 |
| | 8 | −0.292 | 0.086 | (0.0238) |
| | 7 | −1.089 | 0.107 | |
| 4 | 5 | −0.442 | 0.060 | 2.772 |
| | 8 | −0.367 | 0.076 | (0.0057) |
| | 7 | −1.251 | 0.126 | |
| 5 | 5 | −0.370 | 0.048 | 4.428 |
| | 8 | −0.426 | 0.062 | (0.0001) |
| | 7 | −1.340 | 0.094 | |

TABLE 4-continued

| Time (hour) | Formula number | Logarithm of relative decrease | | Determination of synergism |
|---|---|---|---|---|
| | | Mean value | Standard error | t-value (significance probability) |
| 6 | 5 | −0.247 | 0.052 | 4.564 |
| | 8 | −0.577 | 0.086 | (0.0001) |
| | 7 | −1.594 | 0.136 | |
| Area under the curve | 5 | −2.420 | 0.236 | 4.047 |
| | 8 | −1.563 | 0.375 | (0.0003) |
| | 7 | −6.295 | 0.361 | |

(2) Working and Comparative Examples (aerosols)

Aerosols of Formulae listed in Table 5 are prepared, wherein the numerals represent the amounts of the ingredients in grams for 100 ml except otherwise specified and the following abbreviations for the newly entered ingredients are used in addition to the stated ones:
VE: Tocopherol acetate,
IP: Isopropenol,
IM: Isopropyl myristate and
ET: Ethanol.

TABLE 5

| Ingre- | Formula | | | | | | | |
|---|---|---|---|---|---|---|---|---|
| dient | 9 | 10* | 11 | 12 | 13 | 14 | 15 | 16 |
| ES | 2.00 | 1.90 | 2.00 | 2.00 | 2.00 | 2.00 | 2.00 | 2.00 |
| MS | | 3.00 | | | | | | |
| DA | 0.01 | | 0.01 | 0.01 | 0.01 | 0.005 | 0.01 | 0.01 |
| LM | 3.85 | 3.85 | 2.00 | | 3.85 | 3.85 | 3.85 | 3.85 |
| C | | 3.85 | | 3.85 | | | | |
| VE | 0.10 | | 0.10 | | 0.10 | 0.10 | | 0.10 |
| IP | 10 ml | | | | | | | |
| IM | | | | | | | 20 ml | 20 ml |
| ET | | 10 ml | 10 ml | 10 ml | 10 ml | | | 10 ml |

*Formula 10 is a commercially available comparative example.

The measurements on the stated effects (Effects A and B) are made with these compositions in the described manner of evaluation and, in addition to this, ratios of threshold values of pain in adjuvant joint inflammation of the rats (Effct C) i.e., $C = SL/CL$ wherein, SL represents threshold value of pain in the rats of the administered group and CL represents that of the rats of the control group, are also measured to obtain the results shown in Table 6. (means values observed with the eight tested rats)

TABLE 6

| Time (hour) | Formula | | | | | | | |
|---|---|---|---|---|---|---|---|---|
| | 9 | 10 | 11 | 12 | 13 | 14 | 15 | 16 |
| Effect A | | | | | | | | |
| 2 | 42.0 | 35.6 | 36.4 | 29.1 | 25.5 | 27.4 | 27.7 | 32.0 |
| 4 | 46.6 | 17.8 | 40.2 | 45.7 | 45.1 | 38.7 | 51.9 | 61.5 |
| 6 | 50.3 | 8.0 | 49.4 | 57.4 | 51.2 | 48.4 | 63.2 | 64.2 |
| Effect B | | | | | | | | |
| 2 | 42.1 | 26.5 | 56.4 | 70.4 | 66.1 | 58.7 | 67.9 | 61.8 |
| 4 | 58.8 | 20.6 | 65.8 | 62.4 | 64.4 | 51.5 | 64.9 | 74.9 |
| 6 | 60.0 | 20.3 | 66.7 | 68.2 | 69.2 | 50.8 | 69.6 | 78.0 |
| Effect C | | | | | | | | |
| 2 | 1.9 | 1.4 | 1.6 | 1.6 | 1.4 | 1.2 | 1.3 | 1.3 |
| 6 | 1.9 | 1.3 | 1.6 | 1.7 | 1.9 | 1.6 | 2.1 | 1.8 |
| 24 | 2.2 | 1.0 | 1.9 | 2.0 | 2.3 | 1.8 | 2.2 | 2.1 |

As shown in Table 6, the compositions embodying the present invention, as a whole, demonstrate higher effects as compared with the commercially available comparative example (Formula 10) and have made a remarkable improvement in Effects B and C, in particular.

It is further recognized that, by comparing the composition and effect of Formula 13 with those of Formula 14, the persistency in the effects proves to be dependent on the concentration of DA in the compositions.

In the course of conducting the above experiments, it was found that though no difference is observed with the initial effects of the compostions, the stabilities of the active ingredients, in terms of effective contents, are adversely affected by the presence of ethanol as far as DA and ES are used. The fact is confirmed by the test results shown in Table 7 below which is a comparison of Formula 131 tentatively prepared by omitting only ethanol from the ingredients of Formula 13 of Table 5, with Formula 13.

TABLE 7

(Stability of the ingredient in storage, expressed in % content)

| Formula | Ingredient | Months at 40° C. | | |
|---|---|---|---|---|
| | | 1 | 2 | 3 |
| 13 | ES | 100 | 98.0 | 96.3 |
| | DA | 100 | 97.8 | 95.4 |
| 113 | ES | 100 | 99.0 | 100.0 |
| | DA | 100 | 98.0 | 99.0 |

No significant decreases are, however, observed with the initial performance in either of the effects A, B and C as shown in Table 8 below. It is also recognized that no problem may arise from the omisson of ethanol.

TABLE 8

| | Time | Formula | |
|---|---|---|---|
| | | 13 | 131 |
| Effect A | 2 | 25.5 | 33.2 |
| | 4 | 45.1 | 49.8 |
| | 6 | 51.2 | 59.2 |
| Effect B | 2 | 66.1 | 66.9 |
| | 4 | 64.4 | 61.9 |
| | 6 | 69.2 | 64.8 |
| Effect C | 2 | 1.4 | 1.4 |
| | 4 | 1.9 | 2.0 |
| | 24 | 2.3 | 2.5 |

Apart from this, the ingredients of Formula 131 are admixed with any one of trichlorotrifluoroethane, propylene glycol, polyethylene glycol 400 and glycerol by as much as 35 w/w % in order to examine the practicability of the addition for adjusting the viscosity of the thus formed compositions before hermetic sealing with the propellant. As the result of the examination, it is found that the composition including trichlorotrifluoroethane by 35 w/w % is impossible to be sprayed due to the decrease in the internal pressure and that the compositions including any of propylene glycol, polyethylene glycol 400 and glycerol by as much as 15 w/w % or more cannot practically be sprayed due to possible clotting of the spraying nozzle.

(3) Working and Comparative Example (Solutions):

Solutions of Formulae listed in Table 9 below are prepared wherein a similar manner of tabulation is adopted and each solution contains ethanol of the balance in common. Newly used abbreviations are:
TY: Thymol,
CM: Chlorphenamine maleate,
VN: Vanilynonamide,
GL: Glycerol, PG: Propylene glycol,
HL: Hexyl laurate,
OM: Octyl dodecyl myristate and
IA: Diisopropyl adipate.

TABLE 9

| Ingredient | Formula | | | | | | |
|---|---|---|---|---|---|---|---|
| | 17 | 18 | 19* | 20 | 21 | 22 | 23 |
| ES | 2.00 | 2.00 | | 2.00 | 2.00 | 2.00 | 2.00 |
| MS | | | 5.00 | | | | |
| DA | 0.01 | 0.01 | | 0.01 | 0.01 | 0.01 | 0.01 |
| LM | 2.00 | 2.00 | 5.20 | 3.85 | 3.85 | 3.85 | 3.85 |
| C | | | 5.20 | | | | |
| TY | | | 0.70 | | | | |
| VE | 0.10 | 0.10 | | 0.10 | 0.10 | 0.10 | 0.10 |
| CM | | | 0.10 | | | | |
| VN | | | 0.01 | | | | |
| GL | 20 ml | | | | | | |
| PG | | 20 ml | 20 ml | | | | |
| IM | | | | 20 ml | | | |
| HL | | | | | 20 ml | | |
| OM | | | | | | 10 ml | |
| IA | | | | | | | 20 ml |

*Formula 19 is a commercially available comparative example.

Then, measurements on the stated effects (Effects A, B and C) are made by administering the compositions of these Formulae to give the results (means value of the eight tested rats) shown in Table 10. In administering the solutions, site of the edema is first soaked in the solution for 2 seconds, then the excessive solution is wiped out.

TABLE 10

| Time (hour) | Formula | | | | | | |
|---|---|---|---|---|---|---|---|
| | 17 | 18 | 19 | 20 | 21 | 22 | 23 |
| Effect A | | | | | | | |
| 2 | 23.5 | 21.2 | 5.9 | 58.3 | 47.5 | 46.6 | 41.5 |
| 4 | 28.5 | 16.8 | −4.2 | 50.9 | 36.3 | 29.9 | 22.3 |
| 6 | 45.2 | 22.5 | 1.1 | 51.7 | 42.0 | 34.0 | 25.3 |
| Effect B | | | | | | | |
| 2 | 16.7 | 15.8 | 0.5 | 66.7 | 49.5 | 30.5 | 28.4 |
| 4 | 31.3 | 30.9 | 13.0 | 61.5 | 44.2 | 31.3 | 31.7 |
| 6 | 45.8 | 38.4 | −1.0 | 67.8 | 50.0 | 38.1 | 19.5 |
| Effect C | | | | | | | |
| 2 | 1.4 | 1.6 | 1.3 | 1.6 | 1.4 | 1.7 | 1.4 |
| 4 | 1.8 | 1.6 | 1.1 | 1.5 | 1.6 | 1.6 | 1.4 |
| 24 | 2.0 | 1.8 | 1.0 | 2.5 | 2.2 | 2.0 | 1.7 |

As shown in Table 10, all of the compositions embodying the present invention have been found to demonstrate a remarkable effect when compared with the commercially available comparative example (Formula 19). Among the incorporated esters, IM is found to be the most preferred in the points of enhancing effectiveness.

(4) Working Example (Concentrated solution):
ES 200 g, LM 385 g, DA 1 g and VE 10 g are intimately mixed to give 596 g of a concentrated solution (Formula 24). This is portioned into polyethylene eye drop bottles of 10 ml capacity convenient for topical use.

A result of the experiments as regards the disclosed effects (B and C) obtained by comparing the concentrated solution with that of the regular solution (Formula 20) is summarized in Table 11 below. In administering the concentrated solution, its droplet applied on the center of the ailing site is spread with gauze and the excess liquid was wiped out after about one second.

TABLE 11

| | Time | Formula | |
|---|---|---|---|
| | | 20 | 24 |
| Effect B | 2 | 66.7 | 58.8 |
| | 4 | 61.5 | 60.2 |
| | 6 | 67.8 | 66.2 |
| Effect C | 2 | 1.6 | 1.3 |
| | 4 | 1.5 | 1.5 |
| | 24 | 2.5 | 2.8 |

From the above result, Formula 24 is confirmed to be equivalent substantially to Formula 20 in its initial effectiveness and the former is slightly superior to the latter in the persistence of the effects.

(5) Working Examples (Plaster):
Each 10 grams of the above concentrated solution is dispersed to be dissolved into 67.1 g of resinous components of polyisobutylene gum and a silicone gum ("No. 355 MEDICAL ADHESIVE" (trade name) available from Dow Corning Co. Ltd.), respectively, to give paste like products.

These are extended over one side of about 2.0 m² vinyl chloride/vinyl acetate copolymer films in as thick as about 0.05 mm and cut into square strips of 10 mm×10 mm to give plasters (Formula 25 (polyisobutylene) and Formula 26 (silicone)).

The effects (B and C) of the plasters are compared with that of the aerosol (Formula 13) to give the results shown in Table 12 below.

TABLE 12

| | Time | Formula | | |
|---|---|---|---|---|
| | | 13 | 25 | 26 |
| Effect B | 2 | 66.1 | — | 60.3 |
| | 4 | 64.4 | — | 62.5 |
| | 6 | 69.2 | — | 72.3 |
| Effect C | 2 | 1.4 | 1.1 | 1.2 |
| | 4 | 1.9 | 1.5 | 1.6 |
| | 24 | 2.3 | 2.0 | 2.5 |
| | 48 | 1.5 | 1.8 | 2.5 |

Both the plasters are found to be equivalent to the aerosol in the initial effectiveness and superior to the latter in the persistence.

ADVANTAGE OF THE INVENTION

As stated previously, the advantage in terms of industrial availability of the present invention is great because according to the present invention there can be provided the compositions having the stated synergistic effect that persists for a long time as compared with those of either the conventional analgesic anti-inflammatory preparations containing salicylate esters, menthol, camphor and the like as their active ingredients, or the conventional anti-inflammatory preparations containing corticosteroid.

What is claimed is:

1. A topical analgesic anti-inflammatory composition which comprises a mixture of 2–100 parts by weight of ethylene glycol monosalicilate, 0.02–5 parts by weight of a corticosteroid and 10–100 parts by weight of L-menthol.

2. A topical analgesic anti-inflammatory composition as claimed in claim 1 wherein said corticosteroid is dexamethasone acetate.

3. A topical analgesic anti-inflammatory composition as claimed in claim 1 or 2 which is a concentrated solution.

4. A topical analgesic anti-inflammatory composition as claimed in claim 1 or 2 which is a plaster wherein said mixture is contained in at least one of the layers which constitutes the plaster.

5. A topical analgesic anti-inflammatory composition as claimed in claim 1 which contains an effective amount to lower the viscosity of the composition of at least one liquefying agent selected from the group consisting of $C_2$-$C_3$ alkanol, trichlorotrifluoroethane, glycerol, propylene glycol and polyethylene glycol 200-600.

6. A topical analgesic anti-inflammatory composition as claimed in claim 1 which is an aerosol with a non-toxic propellant.

7. A topical analgesic anti-inflammatory aerosol as claimed in claim 6 which comprises:
 (a) ethylene glycol monosalicylate; 0.1-5.0 w/w %,
 (b) dexamethasone acetate; 0.001-0.25 w/w %,
 (c) L-menthol; 0.5-5.0 w/w %,
 (d) tocopherol acetate; 0.05-1.0 w/w %,
 (e) pharmaceutically acceptable excipient; 0.01-0.5 w/w %, and
 (f) non-toxic propellant; necessary amount to make 100 w/w %.

8. A topical analgesic anti-inflammatory aerosol as claimed in claim 6 or 7 which contains 5-20 w/w % of ethanol.

9. A topical analgesic anti-inflammatory composition as claimed in claim 1 which is a solution containing an alkyl ester of a $C_{10}$-$C_{16}$ mono- or di-carboxylic acid.

10. A topical analgesic anti-inflammatory solution as claimed in in claim 9 wherein said alkyl ester of the carboxylic acid is isopropyl myristate.

11. A topical analgesic anti-inflammatory solution as claimed in in claim 9 or 10 which comprises:
 (a) ethylene glycol monosalicylate; 0.1-5.0 w/w %,
 (b) dexamethasone acetate: 0.001-0.25 w/w %,
 (c) L-menthol; 0.5-5.0 w/w %,
 (d) tocopherol acetate; 0.05-1.0 w/w %,
 (e) pharmaceutically acceptable excipient; 0.01-0.5 w/w %, and
 (f) ethanol; necessary amount to make 100 w/w %.

12. A topical analgesic anti-inflammatory composition as claimed in claim 1 which further comprises an effective amount to relax the peripheral vascular system of tocopherol acetate.

13. A topical analgesic anti-inflammatory composition as claimed in claim 1 wherein said corticosteroid is selected from the group consisting of dexamethasone, prednisolone, methylprednisolone, hydrocortisone, betamethasone, triamcinolone and esters thereof.

14. A topical analgesic anti-inflammatory composition as claimed in claim 5 wherein said liquefying agent is present in an amount of 0.1 to 0.5 parts by weight of a concentrated solution.

15. A topical analgesic anti-inflammatory composition as claimed in claim 1 which further comprises 1-20 parts by weight of tocopherol acetate.

* * * * *